US00PP12072P2

(12) United States Plant Patent
Zary

(10) Patent No.: US PP12,072 P2
(45) Date of Patent: Aug. 28, 2001

(54) HYBRID TEA ROSE NAMED 'JACTRIG'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/405,422

(22) Filed: Sep. 22, 1999

(51) Int. Cl.[7] ..... A01H 5/00

(52) U.S. Cl. ..... Plt./138

(58) Field of Search ..... Plt./130, 138

*Primary Examiner*—Howard J. Locker
(74) *Attorney, Agent, or Firm*—Klarquist Sparkman Campbell Leigh & Whinston, LLP

(57) ABSTRACT

A new and distinct variety of rose plant of the hybrid tea class, characterized particularly by its red-purple color; vigorous, upright, well-branched growth; strong, damask rose like fragrance; dark green, glossy foliage; and good disease resistance.

1 Drawing Sheet

The present invention relates to a new and distinct variety of rose plant of the hybrid tea class which was originated by me by crossing the variety 'JACum' (U.S. Plant Pat. No. 5,002), with an unnamed seedling (not patented).

The primary objective of this breeding was to produce a new rose variety combining the strong fragrance of the female parent with the glossy foliage and good disease resistance of the male parent. Flower color was expected to be somewhere between the deep plum of the female and the light lavender of the male. The objective was substantially achieved, along with other desirable improvements, as evidenced by the following unique combination of characteristics that are outstanding in the new variety and that distinguish it from its parents, as well as from all other varieties of which I am aware:

1. Vigorous, upright, well branched growth;
2. Dark green, glossy foliage;
3. Good disease resistance; and
4. Strong, damask rose like fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACum' (U.S. Plant Pat. No. 5,002).

*Pollen parent.*—Unnamed seedling (KORblue (U.S. Plant Pat. No. 3,846)×unnamed seedling (KORblue×unnamed seedling)).

Classification:

*Botanical.*—*Rosa hybrida.*

*Commercial.*—Hybrid tea.

FLOWER

Observations made from specimens grown in a garden environment at Somis, Calif. from March 1997 to December 1998.

Blooming habit: Continuous.

Bud:

*Size.*—1¾ inches long when the petals start to unfurl.

*Form.*—The bud form is long, pointed ovoid.

*Color.*—When sepals first divide, bud color is Red-Purple Group 59B. When half blown, the upper and lower sides of the petals are Red-Purple Group 63D.

*Sepals.*—Color: Green Group 138B with some Greyed-Purple Group 185D on areas exposed to bright sunlight. Surface texture: Covered in fine hairs. There are three heavily appendaged sepals. There are two unappendaged sepals with hairy edges.

*Receptacle.*—Color: Yellow-Green Group 147A. Shape: Funnel. Size: Medium, about ⅜ inch×¼ inch. Surface: Smooth.

*Peduncle.*—Length: Short (about 2 inches). Surface: Smooth, with a few glands. Color: Yellow-Green Group 147B with some Greyed-Purple Group 183A on areas exposed to bright sunlight. Strength: Stiff; erect.

Bloom:

*Size.*—Large. Average open size is about 4½ inches.

*Borne.*—Singly.

*Stems.*—Strength: Strong. Average length is about 16 to 20 inches.

*Form.*—When first open, bloom is high centered. Permanence: flattens; all petals curl.

*Petalage.*—Number of petals under normal conditions: 35.

*Color.*—The upper sides of the petals are Red-Purple Group 63D. The reverse sides of the petals are Red-Purple Group 63D. The base of each petal has on both surfaces a small, ⅜ inch×⅜ inch, Yellow Group 4C color spot. The major color on the upper side is Red-Purple Group 63D.

*Discoloration.*—The general tonality at the end of the first day: No change. At the end of the third day: A change from the bud to ¼ open color of Red-Purple Group 59D to the half open color of Red-Purple Group 63D. By the end of day seven, at the point of petal drop, the color changes to Red-Purple Group 62D.

*Fragrance.*—Strong; damask (old rose scent).

Petals:

*Texture.*—Thin.

*Shape.*—Deltoid.

*Form.*—Tips slightly recurved; edges slightly quilled.

*Arrangement.*—Imbricated. There are no petaloids in the center.

*Persistance.*—Petals drop off cleanly before drying.

*Lastingness.*—On the plant: Long (about seven days). As a cut flower: Long (about eight to nine days).

Reproductive parts:

*Anthers.*—Size: Medium. Quantity: Many. Color: Yellow-Orange Group 15D. Arrangement: Regular around styles.

*Filaments.*—Color: Yellow-Orange Group 16C.

*Pollen.*—Present.

*Styles.*—Color: Yellow-Orange Group 18C.

*Stigmas.*—Color: Yellow-White Group 158A.

Plant:

*Form.*—Bush.

*Growth.*—Vigorous; upright; branching. At maturity, height is five feet, width is four feet.

Foliage: Number of leaflets on normal mid-stem leaves: Five.

*Size.*—Large (6½ inches long×5½ inches wide).

*Quantity.*—Abundant.

*Color.*—New foliage: Upper and lower surfaces: Greyed-Purple Group 183A. Old foliage: Upper surface: Green Group 139A. Lower surface: Green Group 137D.

Leaflets:

*Shape.*—Pointed oval.

*Texture.*—Leathery; glossy.

*Edge.*—Serrated.

*Serration.*—Single; small.

*Petiole rachis.*—Color: Green Group 137D (upper); Yellow-Green Group 147B (lower).

*Petiole underside.*—Smooth.

*Stipules.*—Long (about ¾"); serrated; bearded.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 183A.

*Color when mature.*—Greyed-Orange Group 176A.

Small prickles:

*Quantity.*—On main stalks: None. On laterals: None.

I claim:

1. A new and distinct variety of rose plant of the hybrid tea class, substantially as herein shown and described, characterized particularly by its red-purple color; vigorous, upright, well-branched growth; strong, damask rose like fragrance; dark green, glossy foliage; and good disease resistance.

* * * * *

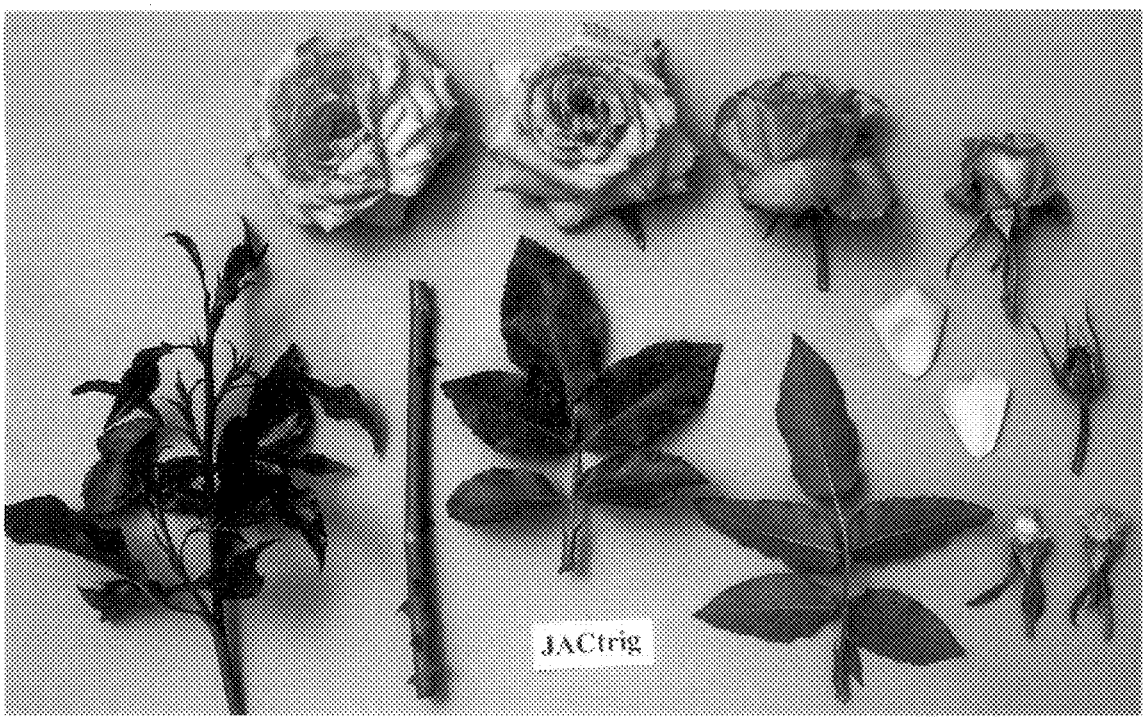
JACtrig